United States Patent [19]

Glabiszewski

[11] 4,007,496
[45] Feb. 15, 1977

[54] CONNECTION BETWEEN A COSMETIC COVER AND A PROSTHETIC PART

[75] Inventor: Richard Glabiszewski, Duderstadt, Germany

[73] Assignee: Otto Boch Orthopadische Industries KG, Duderstadt, Germany

[22] Filed: Sept. 8, 1975

[21] Appl. No.: 611,497

[30] Foreign Application Priority Data

Sept. 16, 1974  Germany ............................ 2444177

[52] U.S. Cl. ............................................. 3/2; 3/12; 3/21
[51] Int. Cl.² ....................... A61F 1/08; A61F 1/06
[58] Field of Search ............... 3/2, 6, 7, 12, 12.2, 3/12.3, 21, 30–35, 1.91

[56] References Cited

UNITED STATES PATENTS

| | | | |
|---|---|---|---|
| 2,422,302 | 6/1947 | Horn | 3/12 |
| 3,659,294 | 5/1972 | Glabiszewski | 3/21 |
| 3,842,442 | 10/1974 | Kolbel | 3/1.91 |

Primary Examiner—Ronald L. Frinks
Attorney, Agent, or Firm—Bosworth, Sessions & McCoy

[57] ABSTRACT

A connection means between a part of a skeletal prosthesis such as a foot or hand and a cosmetic cover. A connecting link is fastened to the open front end of the cover with the surface of the connecting link extending transversely across the front end of the cover. The connecting link has at least two pin sockets running perpendicular and contiguous to its surface with a catch abutting one side of each socket. The link is preferably plate-shaped having a central portion projecting outwardly on one surface and recessed on the other with a central opening to permit passage of a skeletal member. A connecting plate is mounted on the foot or other working part of the prosthesis and has connecting pins for connection with the pin sockets.

4 Claims, 4 Drawing Figures

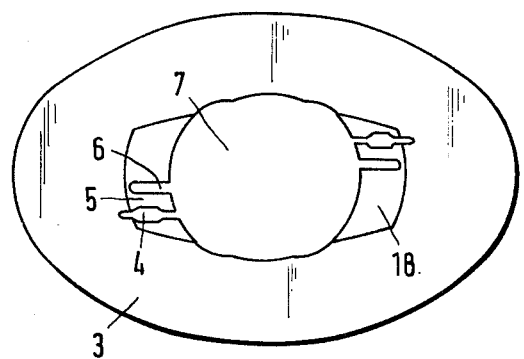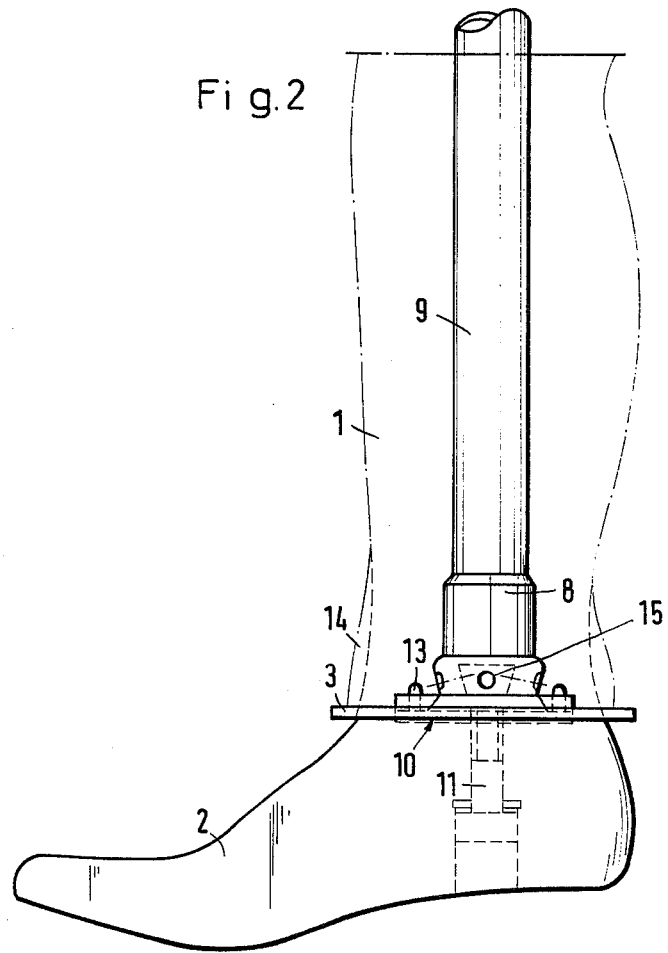

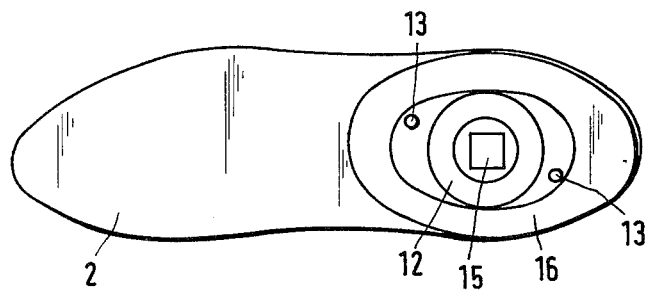
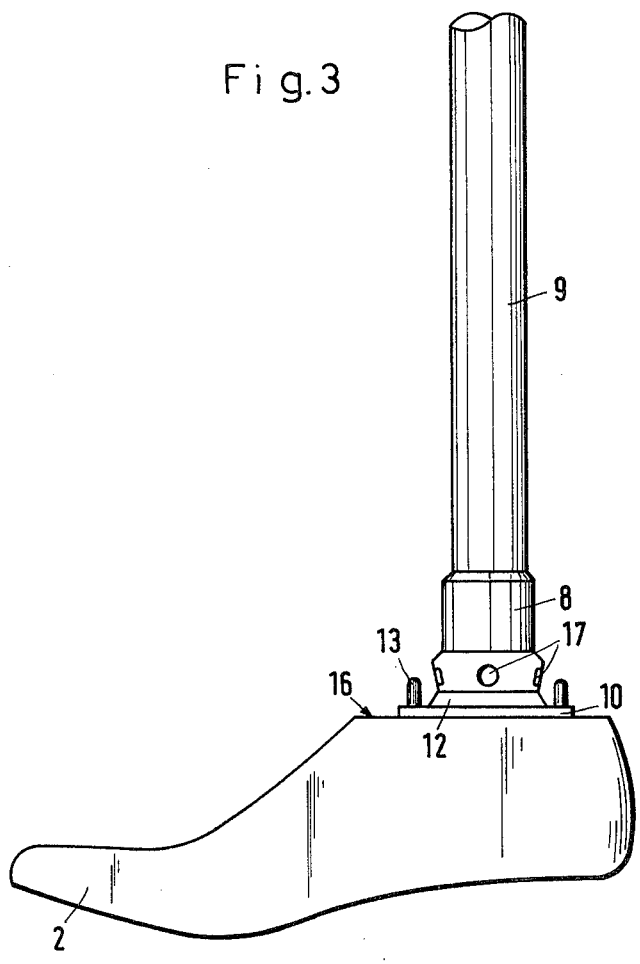

CONNECTION BETWEEN A COSMETIC COVER AND A PROSTHETIC PART

BACKGROUND OF THE INVENTION

This invention concerns a frontal connection between a cosmetic cover — preferably made of foam rubber — and a solid wooden, plastic or similar part of skeletal prosthesis, such as a foot or hand part.

Present-day prostheses consist of a bearing skeleton, e.g., a tubular skeleton, and a molded cosmetic cover made of synthetic material, usually foam rubber. For the coupling of the functional parts, for example foot and knee joint or hand and forearm joint, to the tubular skeleton, adjustable connecting links are used. The bonding of a cosmetic cover to, for example, a foot is accomplished by gluing the frontal end of the cover directly to the foot part or by inserting the frontal end into a hollow space provided inside the foot.

The disadvantage of glued adhesion lies firstly in the fact that in case of repair or readjustments of the skeleton, or when exchange of the foot part becomes necessary, the adhesion surface must be cut open, thus damaging the cosmetic cover. In this instance, renewed gluing is difficult and the cosmetic effect is greatly reduced.

The insertion of the cosmetic cover into a hollow space is of disadvantage because a sufficiently tight hold cannot be achieved and the unavoidable formation of creases greatly reduces the cosmetic effect.

SUMMARY OF THE INVENTION

An object of this invention is to improve the above-described frontal connection in such a way that the cosmetic cover can simply and quickly be loosened and fastened whenever necessary without sustaining any damage.

The object is attained according to this invention through the provision of a connecting link, preferably plastic, fastened as by gluing or welding to the frontal end of the cosmetic cover. This plate-shaped connecting link has two pin sockets running perpendicular to the plate. These pin sockets snap around two pins provided in the prosthetic part and can easily be snapped off again.

The connection is easily made by pressing the frontal end of the cosmetic cover on the pins of, e.g. a foot part, thus achieving a snap-on connection. The parts can easily be disconnected simply by pulling off the connecting part. Inasmuch as the connecting plate can be fitted exactly to the contour of the connecting surface of the foot part (or any other skeletal part), a well fitting cover without formation of creases is assured.

The connecting plate is preferably made from an easily handled synthetic. This makes possible a proper fit with the unfinished cosmetic cover after the completion of the frontal connection. The unfinished connecting plate can thus always have the same shape, independently of the various shapes and sizes of the prosthetic parts that are to be covered, provided that the method of connecting the skeletal member and the functional parts remains the same.

A further advantage is found in the fact that the connecting plate contributes to the stabilization of the frontal end of the cosmetic cover inasmuch as it is preferably made of the softest possible foam rubber material. Finally, the snap-on connection assures a return to the original position each time the cosmetic cover is snapped into place.

To improve the clamping effect of the snap-on connection it is recommended to provide a catch for at least one of the pin sockets. In case of an immovable linkage between skeleton member and the functional part (e.g., foot), the connecting link may be plate-shaped and be provided with an opening for a connecting piece of the skeletal member to pass through.

Preferably, the pins for the snap-on connection sit on another connecting plate which is held in place by an anchor screw inside the foot part and is fastened to the connecting piece of the skeletal member in such a manner that it can be removed easily.

BRIEF DESCRIPTION OF THE DRAWINGS

FIG. 1 is a top view of a plate-shaped connecting link according to the present invention.

FIG. 2 is a side view in a reduced scale of a frontal connection between the cosmetic cover (dotted line) and a foot part.

FIG. 3 is a side view according to FIG. 2 but without the cosmetic cover and its connecting link.

FIG. 4 is a top view of a connecting plate mounted on the flat connecting surface of the foot part.

DESCRIPTION OF A PREFERRED EMBODIMENT

Referring now to the drawings, FIG. 4 shows a foot part 2 with a flat connecting surface 16 on which lies connecting plate 10 held in place by an anchor screw 11 inside the foot part (shown in dotted lines in FIG. 2). FIGS. 3 and 4 show a spherically convex base 12 rigid with connecting plate 10. In the center of this base 12 there is a central boss 15 of frustropyramidal configuration which is shown in FIG. 2 in dotted lines and is rigid with the connecting plate 10. This central boss has four sides, slightly concave as shown in FIG. 2. The connecting plate also holds two pins 13.

FIG. 3 shows the foot part according to FIG. 4 with a skeletal member 9 mounted on the central boss 15 by means of a connecting piece 8. The latter is in form of an annular socket whose concave lower ring surface has the same radius of curvature as the convex base 12 and slidably hugs the latter. The four sides of the central boss 15 are engaged by the tips of respective setscrews 17 threaded into the annular socket of connecting piece 8. Such a connection method is described in U.S. Pat. No. 3,659,294.

FIG. 2 shows a frontal connection between the foam rubber cosmetic cover 1 and the foot part 2 by means of a plateshaped connecting link 3 shown in FIG. 1 in an increased scale and which has been glued or welded to the frontal surface of the cosmetic cover. Connecting link 3 has two pin sockets 4 perpendicular and contiguous to the connecting surface, abutted on one side by a catch 5. To provide vibrating leeway for the latter, a slot 6 is cut therein. In addition, connecting link 3 has an opening 7 to allow passage of the connecting piece 8 of the skeletal member 9. Furthermore connecting link 3 shows a recess 18 whose configuration corresponds to the shape of connecting plate 10. The latter perfectly fits into the recess 18 when the cosmetic cover 1 together with its connecting link 3 is put up on the skeletal member 9. In addition, the two pins 13 of connecting plate 10 are being clasped by the pin sockets 4.

The bulging parts of the cosmetic cover 1 that appear in FIG. 2 as 14 will disappear after the finishing process on the raw cover. In this finishing process the connecting link 3 simultaneously gets its final contours, thus resulting in a tight fit with both the cover 1 and the foot part 2. The extended rim of connecting link 3 which is clearly visible in FIG. 2 is thus eliminated by the finishing process.

What is claimed is:

1. Connection means between a cosmetic cover and a working part of a skeletal prosthesis comprising a connecting link fastened to the front end of said cosmetic cover with the surface of said link extending transversely across said front end, said link having at least two pin sockets that are contiguous to and run perpendicular to the connecting link surface, and connecting pins on said working part for connection with said pin sockets in such a way that said pin sockets are readily removable from said pins.

2. Connection means as claimed in claim 1 further comprising a catch on said connecting link for bracing said pin sockets on at least one side.

3. Connection means as claimed in claim 1 wherein said connecting link is plate-shaped and is provided with an opening to permit passage of a skeletal member associated with said working part to pass through.

4. Connection means as claimed in claim 1 wherein said pins are supported on a connecting plate and further comprising an anchor screw for fastening said plate to said working part and means for removably connecting said connecting plate to a skeletal member associated with said working part.

* * * * *

UNITED STATES PATENT AND TRADEMARK OFFICE
CERTIFICATE OF CORRECTION

PATENT NO. : 4,007,496
DATED : February 15, 1977
INVENTOR(S) : Richard Glabiszewski It is certified that error appears in the above-identified patent and that said Letters Patent are hereby corrected as shown below:

Correct name of Assignee to read as follows:

OTTO BOCK ORTHOPADISCHE INDUSTRIE KG

Signed and Sealed this

Third Day of May 1977

[SEAL]

Attest:

RUTH C. MASON
*Attesting Officer*

C. MARSHALL DANN
*Commissioner of Patents and Trademarks*

Disclaimer

4,007,496.—*Richard Glabiszewski*, Duderstadt, Germany. CONNECTION BETWEEN A COSMETIC COVER AND A PROSTHETIC PART. Patent dated Feb. 15, 1977. Disclaimer filed Aug. 29, 1983 by the assignee, *Otto Bock Orthopadische Industrie KG*.

Hereby enters this disclaimer to claims 1 through 4 of said patent.

[*Official Gazette January 8, 1985.*]